US006696090B1

(12) United States Patent
Nilsson et al.

(10) Patent No.: US 6,696,090 B1
(45) Date of Patent: Feb. 24, 2004

(54) ELECTRO-POWDER

(75) Inventors: Thomas Nilsson, Mariefred (SE); Lars-Gunnar Nilsson, Koping (SE)

(73) Assignee: Microdrug AG, Hergiswil (CH)

( * ) Notice: Subject to any disclaimer, the term of this patent is extended or adjusted under 35 U.S.C. 154(b) by 182 days.

(21) Appl. No.: 09/636,548

(22) Filed: Aug. 11, 2000

(30) Foreign Application Priority Data

Aug. 4, 2000 (SE) ............................................. 0002822

(51) Int. Cl.[7] ............................ A61K 9/14; A61K 9/16; B01J 13/02

(52) U.S. Cl. ....................... 424/489; 424/490; 424/491; 424/497; 424/498; 264/4; 264/4.1; 264/4.32; 264/4.33

(58) Field of Search ................................ 424/489, 490, 424/491, 497, 498; 264/4, 4.1, 4.32, 4.33; 436/149

(56) References Cited

U.S. PATENT DOCUMENTS

| | | | | |
|---|---|---|---|---|
| 4,590,206 | A | * | 5/1986 | Forrester et al. ............ 514/456 |
| 5,830,853 | A | * | 11/1998 | Backstrom et al. ............ 514/4 |
| 5,858,099 | A | * | 1/1999 | Sun et al. .................... 118/621 |
| 5,952,008 | A | * | 9/1999 | Backstrom et al. ......... 424/499 |
| 6,138,671 | A | * | 10/2000 | Noakes et al. ......... 128/202.25 |
| 6,214,300 | B1 | * | 4/2001 | Morrison et al. ........... 422/238 |
| 6,245,339 | B1 | * | 6/2001 | Van Oort et al. ........... 424/400 |
| 6,328,033 | B1 | * | 12/2001 | Avrahami .............. 128/203.15 |
| 6,406,745 | B1 | * | 6/2002 | Talton ........................ 427/213 |
| 2002/0176926 | A1 | * | 11/2002 | Pletcher et al. ............ 427/2.14 |

* cited by examiner

*Primary Examiner*—Thurman K. Page
*Assistant Examiner*—S. Tran
(74) *Attorney, Agent, or Firm*—Young & Thompson

(57) ABSTRACT

A method and a process are disclosed for preparation of medical electro-powders. The electro-powder results from preparations of chemical and biological substances to form electro-powders suitable for electrostatic charging and dosing for functionality in a dry powder inhaler device. The electro-powder resulting from the method and process forms an active powder substance or a dry powder medical formulation with a fine particle fraction representing of the order 50% or more of the content having a size ranging between 0.5–5 μm and provides electrostatic properties with an absolute specific charge per mass after charging of the order $0.1\times10^{-6}$ to $25\times10^{-6}$ C/g and presenting a charge decay rate constant $Q_{50}>0.1$ sec with a tap density of less than 0.8 g/ml and a water activity $a_w$ of less than 0.5. In the processing the active substance is a generally pharmaceutical active chemical or biological substance, for instance a polyeptide or any other corresponding substance selected alone or mixed or blended together with one or more excipients being a compound to improve electrostatic properties of the medical dry powder substance or dry powder medical formulation. Further the electro-powder may even be formed as a micro-encapsulation by coating micronized powder with the excipient in such a way that the active substance is capsulated, whereby the powder electrostatic properties mainly comes from the excipient.

9 Claims, 8 Drawing Sheets

ELECTRO-POWDER

TECHNICAL FIELD

The present invention relates to powders with electrostatic properties as well as a process and a method for preparation of such an electro-powder as a s medical powder and more particularly to preparations of chemical and biological substances forming an electro-powder suitable for electrostatic charging and dosing for functionality in an inhaler device.

GENERAL BACKGROUND

Today high quality dosing is one of the most difficult factors slowing down the growth of the inhaler market. This is specially the case for systemic delivery by inhalation through a dry powder inhaler (DPI) which represents a market segment making it possible to compete with the injection needle for many types of drugs, i.e. insulin, pain management etc. Systemic delivery refers to the delivery of an active substance to be carried to a deep area of the lung. U.S. Pat. No. 5,997,848 discloses a systemic delivery of insulin to a mammalian host being accomplished by inhalation of a dry powder of insulin. An insulin dose 0.5 to 15 mg is dispersed into a high velocity air or gas stream to form a dry insulin aerosol in a holding chamber from which the created aerosol is inhaled. The volume of the chamber has to be sufficiently large to capture a desired dose and may optionally have baffles and/or one-way valves for promoting containment. Such a device is often referred to as a spacer. The device for instance has a drawback in that there are difficulties to control the amount of medicine emitted to the lung as an uncontrolled amount of powder will stick to the walls of the spacer.

A dry powder inhaler, DPI is intended for administration of powder into the deep or upper lung airways by oral inhalation. With deep lung should be understood the peripheral lung and alveoli, where direct transport of active substance to the blood can take place. Particle sizes, to reach into the deep lung, should be in the range 0.5–3 μm and for a local lung delivery in the range 3–5 μm, as measured with a laser diffraction instrument, e.g. a Malvern Mastersizer for physical size classification or an Andersen Impactor for an aerodynamic size classification according to US Food and Drug Administration (FDA) current guidelines.

Powders for inhalers have a tendency of agglomerating, in other word to clod or to form small or larger lumps, which then have to be de-agglomerated. De-agglomeration is defined as breaking up agglomerated powder by introducing electrical, mechanical, or aerodynamic energy. Usually de-agglomeration is performed as a step one during dosing and as a final step two during the patient's inspiration through the DPI.

Technologies to de-agglomerate today include advanced mechanical and aerodynamic systems and combinations between electrical and mechanical filling systems that can be seen in for instance in U.S. Pat. No. 5,826,633. Further there are systems disclosed for dispersing aerosolized doses of medicaments, e.g. U.S. Pat. No. 5,775,320, U.S. Pat. No. 5,785,049, and U.S. Pat. No. 5,740,794. Furthermore, in our International Publications WO 00/0636 and WO 00/6235 principles for de-agglomeration and classification are disclosed.

As already noted for an optimal amount of substance to reach the alveoli, an administered powder dose should preferably have a grain size between 0.5 and 3 μm. Besides, the inspiration must take place in a calm way to decrease air speed and thereby reduce deposition in the upper respiratory tracts.

Mainly particles larger than 5 μm will be deposited in the upper airways by impaction and particles less than 0.5 μm will not sediment before exhaling and therefore not being efficient for delivery to upper or deep lung.

It is also common to utilize carriers i.e. Lactose having a larger grain size onto which the fine power is distributed. Upon inspiration the large size grains will then stick in the oral cavity while the fine particle fraction, this is powder smaller than 5 μm, will be let free and proceed to the lung. For instance U.S. Pat. No. 5,642,727 discloses a tribo-inhaler having a container portion for electrostatically retaining a predefined dose of medicament powder. The container portion contains a plurality of polymeric beads that have diameters of approximately 50 to 200 microns. Each of the polymeric beads has a specific quantity of dry powder medicament electrostatically adhered to its surface.

To achieve a high quality dose, a so-called spacer is often used to achieve the small grains evenly distributed in a container from which the inhalation can take place. In principal a dosing device or an inhaler is connected to a spacer forming a container having a relatively large volume and into this container a powder or an aerosol is injected, which partly is distributed in the air space and partly sticks to the walls. Upon inhalation from the spacer the fine powder floating free in the air will effectively reach the alveoli of the lung. This method in principle has two drawbacks, firstly difficulties to control the amount of medicine emitted to the lung as an uncontrolled amount of powder sticks to the walls of the spacer and secondly difficulties in handling the relatively space demanding apparatus. The uncontrolled sticking to the walls is highly dependent on the electrostatic charge of the medical powder.

Today dosing into cavities for inhalation through a dry powder inhaler (DPI) is performed by using mechanical, fluidization and electrical technologies in combinations to fill cavities with powder intended for inhalation by patients. One example of this technique is the already mentioned U.S. Pat. No. 5,826,633 in which a combination of fluidization and mechanical forces is used to fill a cavity with a metered dose.

This type of technique will give a dose that will need a lot of energy to de-agglomerate before inhalation into the deep lung. This is performed using a mechanical pump that is actuated before inhalation and a high-pressurized air stream is shot down into the powder for de-agglomeration into a cylindrical spacer. Inhalation efficiency for this type of system is normally not more than 20% of metered dose.

One major problem with some of the technique described above is to also obtain a low relative standard deviation (RSD) between doses with this type of technique due to lack of in-line control possibilities in production making it hard to be in compliance with regulatory demands.

Different commercial manufacturing equipment are today present on the market, i.e. equipment used to produce micronized powders working with specialized nozzles for creating liquid or semisolid aerosols, which are dried to powders. The equipment can also be used for coating-techniques and Cryo-techniques to produce low-density powders. Fluid Jet Mill equipment is used to produce micronized powders by working with high-pressurized gases, normally air or nitrogen. Also solvents defined as liquids are used to dissolve or disperse active substances and excipients, e.g. alcohols, before sprayed into the manufacturing equipment or other gases such as carbon dioxide, chlorofluorocarbons or eqivalent, perfluorocarbons, air or other suitable inert gas for the manufacturing equipment can be used. Such equipment also can be used for purposes of coating, drying and Cryo-techniques, one at a time or in combinations, where Cryo-techniques is a method in which super cold media, i.e. liquid nitrogen or carbon dioxide, is used for cooling down the manufacturing equipment and the preparation below 0° C. Blending is defined as a homogeneous mixture of at least one active substance and one or many excipients regardless of amounts and particle sizes, and can be used alone or in combinations with spray drying and Fluid Jet Milling to prepare an electro-powder. By the term excipient is meant a chemical or biological substance introduced together with a pharmaceutical active substance to, for instance, improve the performance of the preparation or is an compound intended to act as an inactive surface and/or volume suitable for the active substance normally being a mix preferably chosen among the available excipients not to deteriorate the powder properties of the preparation.

Micronized medical powders are being electrostatically charged in many occasions in the pharmaceutical industry whereby this creates a big problem by causing stops and producing dust on surfaces that should be kept clean.

When electrostatic properties of a micronized medical powder is controlled this can be used to present an efficient and high quality dosing from electrostatically operating equipment such as disclosed in our U.S. Pat. No. 6,089,227 as well as our Swedish Patents No. 9802648-7 and 9802649-5, which present excellent inhalation dosing performance.

An International Publication WO 00/35424 discloses a substrate coating for electrostatic deposition of dry powder medicaments for use in the manufacture of pharmaceutical dosage forms. The dry powder comprises micronized polyethylene glycol (PEG), with a molecular weight of 1,000 to 20,000. However, the particles are stated to have a size of 1–100 μm and a preferred size is claimed for 5–20 μm but there is nothing told about the fine particle fraction or the specific charge of a fine particle fraction.

However, there is still a need for a much more developed control of the electrostatic charging quality of applicable medical powders before they are going to be used in electrostatic dosing equipment.

SUMMARY

The present invention makes it possible for a majority of dry medical substances to be prepared by using the method and process of the present invention to obtain a medical dry powder, "electro-powder", suitable for electrostatic charging and dosing. The electro-powder thus obtained will be possible to dose with high efficiency and quality by electrostatic dosing equipment.

A method and a process for preparation of medical powders for electrostatic charging are disclosed. An electro-powder results from preparations of chemical and biological substances to form powders suitable for electrostatic charging and dosing for functionality in a dry powder inhaler device. The electro-powder resulting from the method and process forms an active dry powder substance or dry powder medical formulation with a fine particle fraction (FPF) representing of the order 50% or more of the content ranging between 0.5–5 μm and provides electrostatic properties with an absolute specific charge per mass after charging of the order 0.1 to 25 μC/g and presents a charge decay rate constant $Q_{50}$ of more than 0.1 s, and having a tap density of less than 0.8 g/ml and a water activity $a_w$ of less than 0.5. In the processing the active substance is generally a pharmaceutical active chemical or biological substance, for instance a polyeptide, or any other corresponding substance selected alone or mixed or blended together with one or more excipients being a compound to improve electrostatic properties of the medical powder substance or dry powder medical formulation. Further the electro-powder may even be formed as a micro-encapsulation by coating micronized powder with the excipient in such a way that the active substance is capsulated, whereby the powder electrostatic properties mainly comes from the excipient.

A method for producing electro-powder according to the present invention is set forth by the independent claim 1 and further embodiments are set forth by the dependent claims 2 to 7, a process for acquiring the electro-powder is set forth by the independent claim 8 and further embodiments of the process are set forth by the dependent claims 9 to 23. Finally an electro-powder according to the present invention for use with a dry powder inhaler is set forth by the independent claim 24 and the dependent claims 25 to 40.

BRIEF DESCRIPTION OF THE DRAWINGS

The invention, together with further objects and advantages thereof, may best be understood by making reference to the following description taken together with the accompanying drawings, in which.

DESCRIPTION

Figure 1:
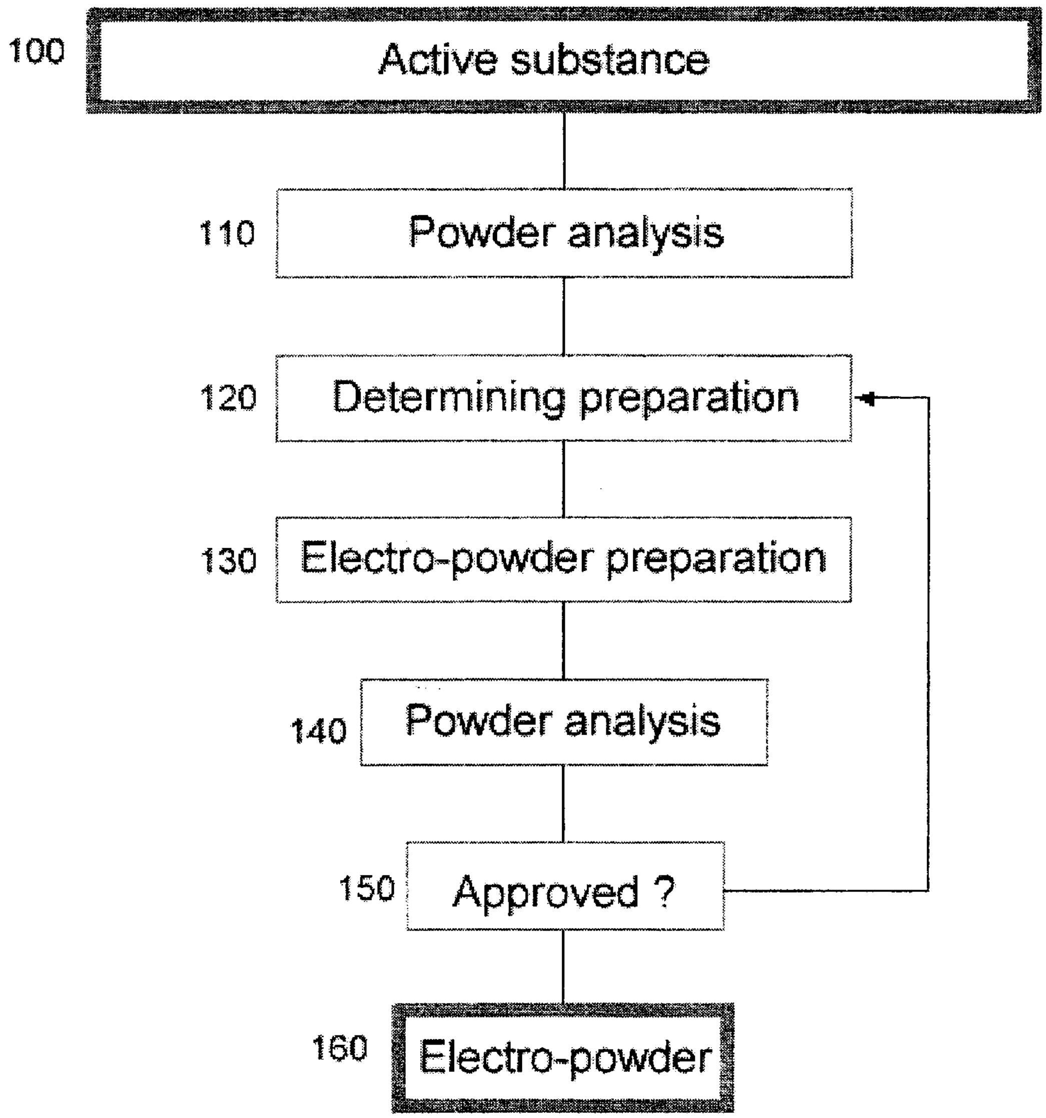
FIG. 1 illustrates an alternative for a general structure of the method according to the present invention for obtaining high quality electro-powder.

Electrostatic charging of medical powders is a new technology making it possible to dose by the use of controlled electrical field techniques. A field created as different electrical potentials is intended for in a controlled way transporting electrostatically charged powder for dosing or measuring purposes. The electrostatic charging may be performed by means of corona, induction or tribo-electrical charging.

An electro-powder is defined as a fine powder prepared to meet a set of electrical specifications and other specifications. Such an electro-powder is, after a proper processing, expected to present an electrical specification measured at room temperature with an absolute specific charge of the order of 0.1 to 25 $\mu$C/g ($0.1\times10^{-6}$–$25\times10^{-6}$ Coulomb/gram of negative or positive charge) and desired to present a charge decay constant $Q_{50}$ of >0.1 sec, where $Q_{50}$ is defined as the time until 50% of the electrostatic charge is discharged, (for instance after a corona charging in an Electrical Low Pressure Impactor (ELPI) model 3935 from DEKATI LTD).

The electrostatic charged micronized powder, defined as electro-powder, should in the desirable process be prepared such that at least more than 50% of the present powder particles have a particle size below 10 $\mu$m. According to the present invention such electro-powder is produced in an equipment simultaneously making a preparation and measuring the quality of produced dry powder for electrostatic charging. For instance Fluid Jet Mill and/or Spray Drying and/or Cryo-techniques or microwave drying will be used as well as blending, or any other suitable process. However, in the industry today according to the state of the art the processes are not fully controlled and the powder may at some occasions show a positive charge and at other occasions a negative charge. These differences in the behavior are due to that the pharmaceutical industry generally does not know how to keep the electrostatic and powder properties under a strict specification and control.

In order to be able to use inhalation to provide administration of a medicament and in this manner replace needle injection of medicine the electro-powder have to possess the right properties. Measured at room temperature the electro-powder is expected to contain more than 50% of fine particle fraction (FPF) and to have a water content of less than 4% together with a water activity $a_w$ less than 0.5 and a tap density of less than 0.8 g/ml. The water content is the total amount of water in the powder sample in percent of weight using for instance a Karl-Fischer titration or any equal method. Water activity $a_w$ is a dimensionless quantity, which may, for instance, be measured with an AquaLab model series 3 TE. Tap density is, for instance, measured by using a Dual Autotap from Quantachrome© Corporation according to British Pharmacopoeia for Apparent Volume method. Both water activity and tap density are quantities well know to a person skilled in the field of chemistry analysis. The electrostatic properties, defined as the amount of electrostatic charge that the powder holds after a corona, induction or tribo-electrical charging, are critical and should meet the electrical specification, which is measured with an electrometer in $\mu$C/g at room temperature 18° C. to 25° C. in an air or nitrogen atmosphere with a relative humidity of less than 5%. As electrometer may for instance be utilized a Keithley Electrometer 6512.

The fine particle fraction represents the aerodynamic particle size measured for instance with an Andersen Impactor. The physical size can vary due to density and aerodynamic properties of the medical powder, e.g. super porous particles with a tap density of <0. 1 g/ml.

The preparation of an electro-powder for an inhaler device includes the manufacturing of the medical powder by particular equipment using one or more active substances.

Consequently, to be able to dose and administer powder using a dry powder inhaler (DPI), some quite important technical basic conditions must be met by the used powder:

a) A powder having a very fine particle fraction (FPF) must be prepared as it is generally only particles between 0.5 and 3 $\mu$m that will be medically active by being transported to the deep lung. For local lung treatments by inhalation the particle size should be between 3–5 $\mu$m.

b) A correct dose and a low dose-to-dose relative standard deviation (RSD) must be released from the inhaler. For electrostatically dosed dry powders with electrostatic properties inside set specification the relative standard deviation between doses (RSD) will not be more than 2–4%.

c) Electrostatic properties of the powder must be specified and controlled before and during dosing to ensure the right medical quality of electrostatically dosed powder.

d) Water content, measured as Karl-Fischer moisture content, should be below 4%.

e) Powder water activity $a_w$ must be very low and less than 0.5 and controlled to enable a high quality and amount of electrostatic charge measured as Q/m ($\mu$C/g) (charge/mass of powder).

f) Thus, water activity $a_w$ is a key factor and must be below 0.5 and controlled by having an environment, which is kept at a very low relative humidity, most preferably below 5% at 18–20 C.

The administration of electro-powder into the respiratory tract is then a very attractive way for administration of many substances both for local lung treatments and for systemic treatments.

The amount of electrostatic charge per mass of the medical electro-powder should be within a certain range to achieve a good control of the dosing process for the electrostatic dosing process. This range for the absolute charge per mass with a medical dry powder with a fine powder fraction between 0.5 and 5 $\mu$m would desirably range from 0.1 to 25 $\mu$C/g dependent on the type of constituents.

Micro-encapsulation is defined as a coating of a micronized powder with an excipient in such a way that the active substance is capsulated and the powder properties manly comes from the excipient. This is also a very efficient preparation method for difficult active substances, for which the electrical specifications of electro-powder otherwise are difficult to meet.

Therefore preparation may be chosen in combination with micro-encapsulation and/or chosen together with one or more excipients.

In FIG. 1 is schematically illustrated the basic principle of the method according to the present invention to achieve a high quality dry powder to be electrostatically charged, mainly referred to as just electro-powder, for utilization in a dry powder inhaler (DPI).

Many active substances will be of interest to use for local lung delivery or systemic delivery. The active substance is generally a pharmaceutical active chemical or biological substance intended for administration into the deep or upper lung airways by oral inhalation from the DPI. In FIG. 1 step 100 a substance would for instance be macromolecules from the following therapeutic areas: insulin rapid intermediate and slow acting and diabetes peptides, interferons, interleukins and antagonists, antibodies, peptides for immune suppression, nerve growth factors, vaccines, gene therapies, genetically modified virons and/or bacterias, parathyroid hormone, osteoporosis peptides, antiobesity peptides, luteinizing hormone releasing hormone (LHRH) and LHRH analogs, somatostatin analogs, human calcitonin, colony stimulating factor, erythropoietins, growth hormones, erectile dysfunction, anti pregnancy hormones.

An active substance is preferably selected from the following pharmaceutical active chemical and biological substances: vasopressin, a vasopressin analogue, desmopressin, glucagon, corticotropin, gonadotropin, calcitonin, C-peptide of insulin, parathyroid hormone, human growth hormone, growth hormone, growth hormone releasing hormone, oxytocin, corticotropin releasing hormone, a somatostatin analogue, a gonadotropin agonist analogue, atrial natriuretic peptide, thyroxine releasing hormone, follicle stimulating hormone, prolactin, an interleukin, a growth factor, a polypeptide vaccine, an enzyme, an endorphin, a glycoprotein, a lipoprotein kinas, intra-cellular receptors, transcription factors, gene transcription activators/repressors, neurotransmitters (natural or synthetic), proteoglycans.

Further could be selected a polypeptide involved in the blood coagulation cascade, and which exerts its pharmacological effect systemically or any other polypeptide that has a molecular weight (Daltons) of up to 50 kDa, or a substance from the group consisting of proteins, polysaccharides, lipids, steroids, oligasaccharides, nucleic acids and combinations thereof or a substance from a group consisting of leuprolide and albuterol or is among opiates or nicotine derivatives or scopolamin, morphine, apomorphine analoges or equivalent active substances or pharmaceutical active chemicals for asthma treatment, i.e. budesonid, salbutamol, terbutalinsulphate, salmeterol, flutikason, formoterol or salts thereof.

Figure 2:
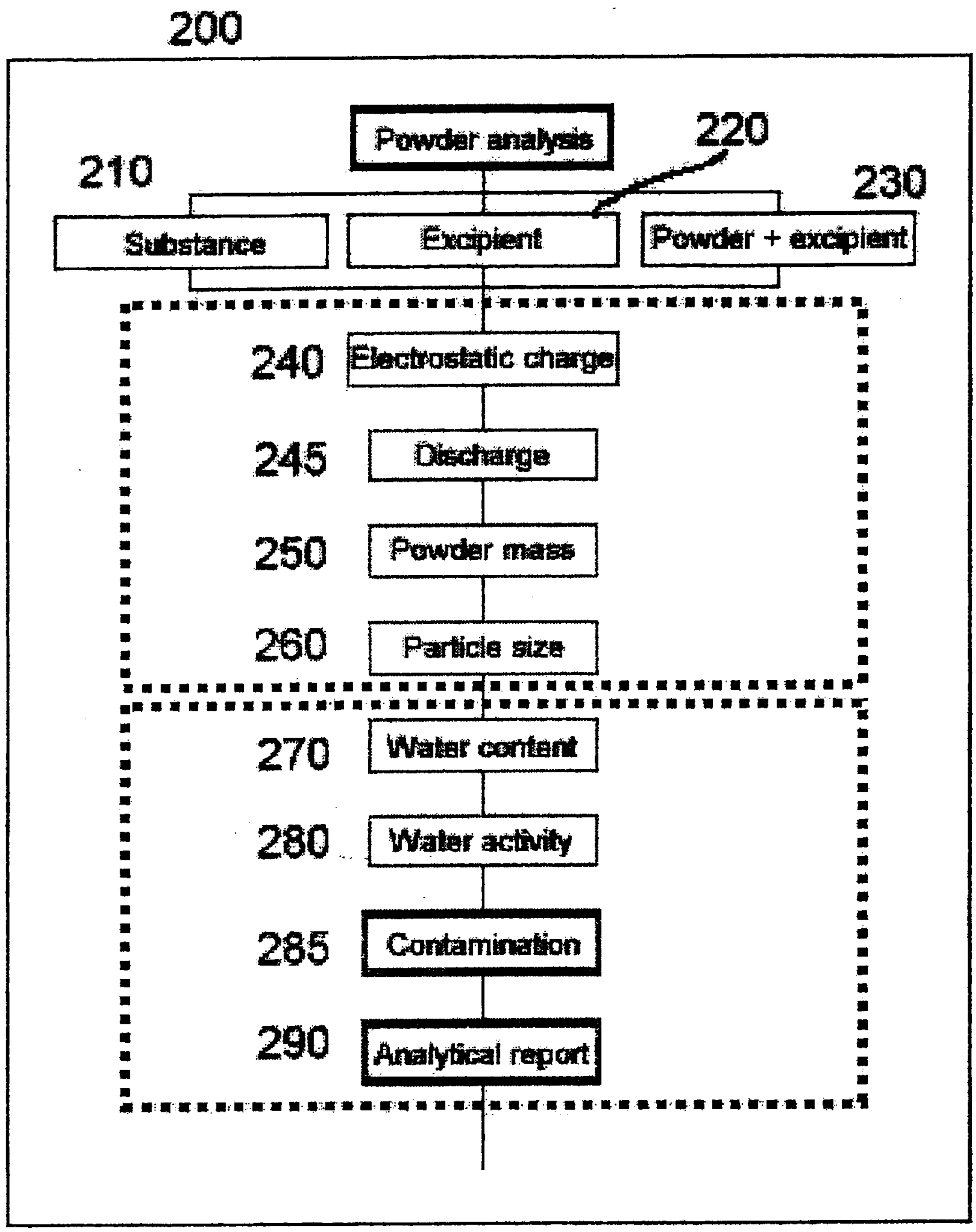
FIG. 2 illustrates an alternative for a powder analyzing method.

Thus, the present method starts at a step 100with an active substance to further go through an electro-powder preparation step 130, to at a step 160 result in a high quality electro-powder to be used in an inhaler. Before the active substance in step 100 will be subjected to a determining of the preparation in a step 120 a powder analyzing step 110 is performed. The power analyzing step 110 is further described by steps 210–290 as illustrated in FIG. 2. The powder analysis will first via any of the steps 210 to 230 analyze either the substance itself or an excipient or the substance and excipient together for determining electrostatic charge in a step 240, powder mass in a step 250, particle size in a step 260, water content in a step 270, water activity in a step 280 and finally produce an analytical report in a step 290 as basis for the determination of the preparation. The result from step 290 then is transferred to step 120 of FIG. 1.

As already noted the term excipient refers to a chemical or biological substance introduced together with the pharmaceutically active substance to improve its electrostatic performance. The excipient or excipients for instance are selected from a group consisting of polyvinyl alcohol, methalose, methyl cellulose, ethyl cellulose, propyl cellulose, hydroxy ethyl cellulose, carboxy methyl cellulose, polyoxyethylene cetyl ether, polyoxyethylene lauryl ether, polyoxyethylene octyl ether, polyoxyethylene octylphenyl ether, polyoxyethylene oleyl ether, polyoxyethylene sorbitan monolaurate, polyoxyethylene stearyl ether, polyoxyethylene nonylphenyl ether, and dialkylphenoxy poly (ethyleneoxy)ethanol, or an anionic surfactant selected from a group consisting of sodium dodecyl sulfate, sodium dodecylbenzene sulfate and sodium dodecylnaphthalene sulfate, glucolipids, phosphoglucolipids.

The excipient may also be a cationic surfactant like a quaternary ammonium salt or selected from the group consisting of dim ethyl-beta-cyclodextrin, dioctanoylphosphatidylcholine, lysophosphatidylcholine, and a salt of caprate, laurate, oleate, or myristate or a salt of ursodeoxycholate, taurocholate, glycocholate, or taurodihydrofusidate, or from a group consisting of an anionic surfactant, a cationic surfactant, a phospholipid, an alkyl glycoside, a cyclodextrin, a salt of capric acid, and a sodium, potassium or organic amine salt of a fatty acid or is a bile salt or selected from homo- and copolymers based on hydroxycarboxylic acids, such as polymers of glycolide, lactide, methylglycolide, dimethylglycolide, polymethylglycolide, diethylglycolide, dibutylglycolide, caprolactone, valerolactone, decalactone, propiolactone, butyrolactone, pivalolactone, as well as polymers based on trioxanone, dioxanone (1,3 and 1,4), substituted dioxanone, trimethylene carbonate, ethylene carbonate and propylene carbonate or lactic acid, glycolic acid, pentaerythritol, sorbitol, adonitol, xylitol, fructose, epichlorohydrin, isopropylmorpholine, isopropylmethylmorpholinedione, β-propionic acid, tetramethylglycolide, β-butyrolactone, butyrolactone, pivalolactone, α-hydroxybutyric acid, α-hydroxyisobutyric acid, α-hydroxyvaleric acid, α-hydroxyisovaleric acid, α-hydroxycaproic acid, α-hydroxyisocaproic acid, α-hydroxy-α-ethylbutyric acid, α-hydroxy-α-methylvaleric acid, α-hydroxyheptanoic acid, α-hydroxyoctanoic acid, α-hydroxydecanoic acid, α-hydroxytetradecanoic acid and α-hydroxystearic acid or is a bio-degradable synthetic polymer i.e. PEG, amino acid derived β-poly(2-hydroxyethyl aspartamide), poly($^5$N-(2-hydroxyethyl)-L-glutamine), poly(glutamic acid), poly (aspartic acid), polylysine, PEG-lysine, or polyesters poly(a or β-malic acid), or block copolymers poly(ethylene glycol-aspartate) also called polymeric micelles or is a liposome forming substance or a natural or synthetic wax or from sugar alcohols i.e. glycerol, sorbitol, or from monosaccarides i.e. fructose, glucose, or from disaccarides i.e. sucrose, maltose, trehalose, lactose, or from trisaccarides i.e. raffinose, or from polysaccarides i.e. dextran, or from oligosaccarides i.e. maltohexose, or from buffering salts i.e. sodium citrate.

Figure 3:
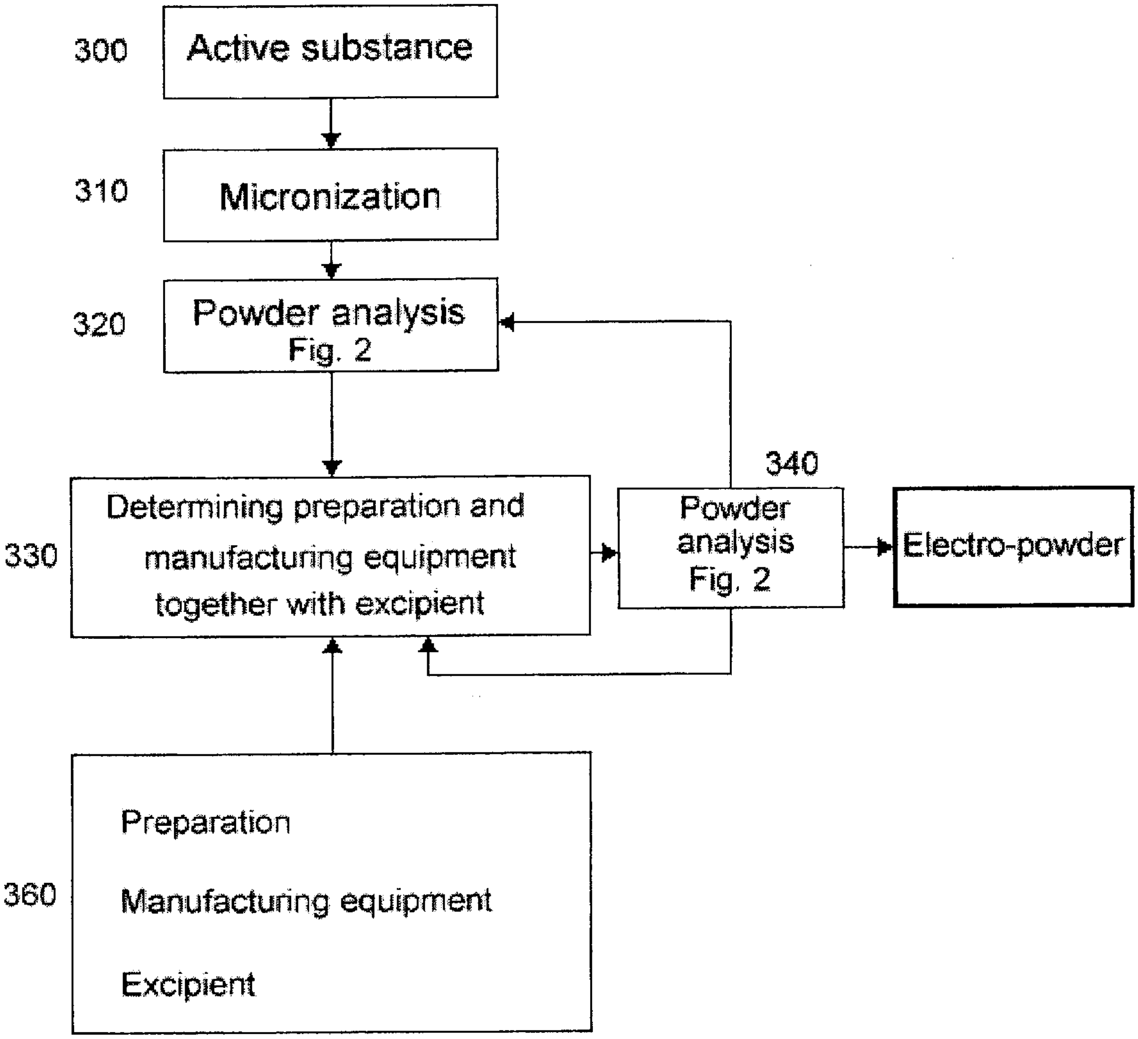
FIG. 3 illustrates an alternative for a method of determining preparation of electro-powder.

In FIG. 3 a further part of the present method is outlined in a step 330 for determining the preparation and manufacturing process together with a selected excipient. FIG. 3 indicates, that the active substance received in step 300 may as a first step have to be micronized in a step 310 and as a second step be subject to powder analyzing in a step 320 before being transferred to step 330 for determining preparation and manufacturing equipment together with selection of possible excipient. The result of the step 330 then goes to a powder analyzing step 340 to determine whether or not the powder meets both the electrical specification and physical specification of an electro-powder. The powder-analyzing step 340 also corresponds to the analyzing process performed in steps 240 to 290 of step 200 of FIG. 2.

In the case, if the powder present in the powder analyzing step 340 is found not to be an approved electro-powder, the process according to the method loops back to steps 320 or 330 for a new determination of preparation and manufacturing equipment together with another possible selected excipient to improve the result of the preparation of the active substance to obtain an electro-powder, which fulfils the basic factors lined up above.

The powder analyzing step 200 of FIG. 2 is used for analyzing active substance in a step 210 and excipients in a step 220 and combinations of active substances and excipients in a step 230 to then determine the electrostatic charge in step 240, powder mass in step 250, particle size in step 260, water content in step 270, water activity in step 280, discharge in step 245 and contamination in step 285 to make it possible to calculate the specific charge and estimating the discharge rate constant to determine if the tested excipient is suitable or another should be selected. However as mentioned same steps 240 to 290 may be used within steps 320 and 340 of FIG. 3.

According to the present process an active substance is tested to obtain a basis for determining preparation and manufacturing equipment together with the excipient to become as efficient as possible. After that the mapping of the active substance and the interesting excipients is done FIG. 1 indicates that the process proceeds to step 120 of determining preparation and the results from the powder analyzing from step 110 will in step 120 be interpreted for determining preparation. From step 120 determining preparation the process then proceeds into the electro-powder preparation step 130 which is illustrated by examples of embodiments presented FIG. 4 and FIG. 5, where FIG. 4 illustrates an Fluid Jet Milling at 400 and FIG. 5 illustrates a Spray Drier at 500.

Figure 4:
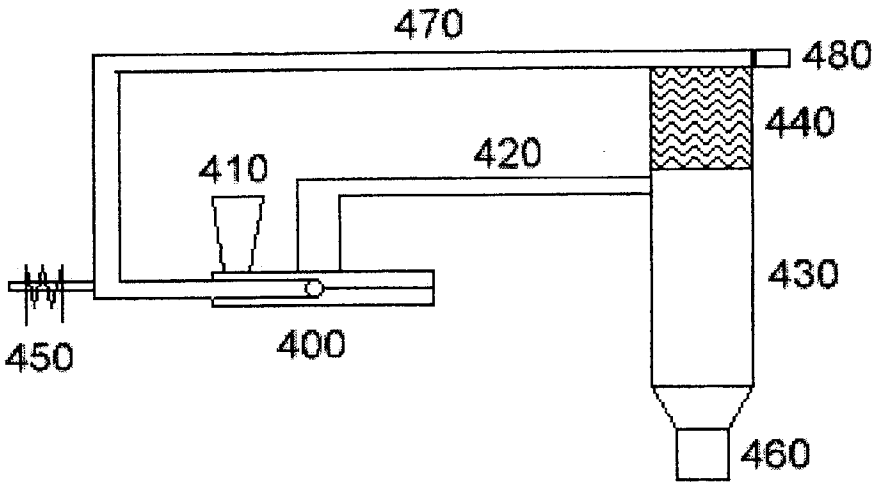
FIG. 4 illustrates a first example of manufacturing equipment.

If the step of determining preparation and manufacturing equipment together with an actual excipient has chosen a Fluid Jet Milling preparation step the process will in an illustrative embodiment proceed as below:

In a sketch of the process, illustrated in FIG. 4, the powder material will be continuously feed into the mill at 410 together with the chosen media and the micronized powder will be feed out at 420 into a cyclone 430 and the resulting air is filtered at 440 before going back into circulation via an feedback arrangement 470 into the mill. It is possible to add an arrangement 450 for material warming up to dry out moisture trapped in the preparation and also bleed out moist media at 480 to continuously have a correct climate for the electro-powder preparation. The electro-powder is then collected for a new analysis after shaking off the filters at 440 into the dry powder container indicated at 460.

Figure 5:
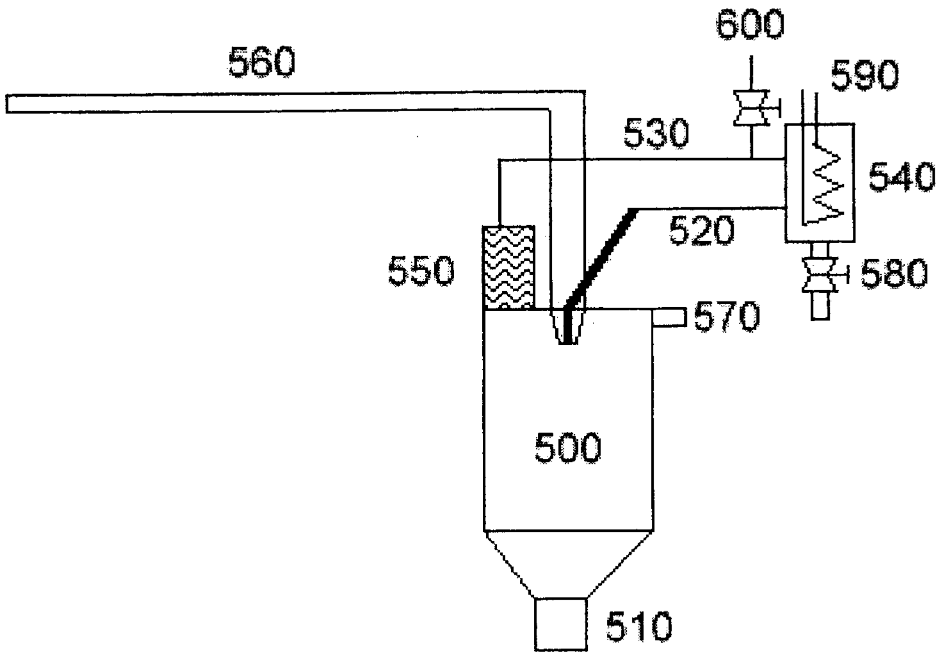
FIG. 5 illustrates a second example of manufacturing equipment

FIG. 5 illustrates schematically a Spray Drier 500 where the preparation is feed at 560 into the Spray Drier. Before entering the Spray Drier 500 the preparation will be atomized by a pressurized media 520 and dried to an electro-powder via a classification process and collected in the dry powder container 510. The injected media is going back into circulation via a filter 550 and clean air is let out of the system at 530. New media 600 is possible to be warmed up at 590 to have a even better dying effect on the electro-powder collected in the dry powder container 510. If a closed loop system with a media that is not air the media going through the filter must be cleaned 540 and circulated back into the system after cleaning step 530. If a closed loop system is used, the system moisture is controlled by means of a means 570 discarding the moist and new processing media is introduced at 600.

Figure 6:
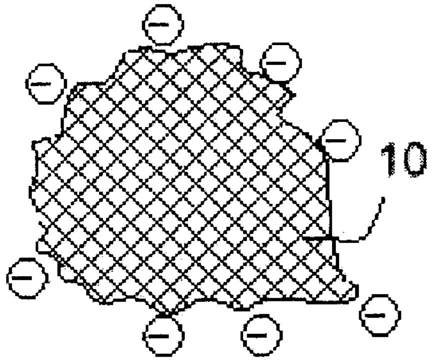
FIG. 6 illustrates in a cross section a first example of an electro-powder presenting an electrostatic charged surface.

The result of the above methods will be an electro-powder that can have different appearance depending of how the electro-powder is prepared if looking at a cross section of an electro-powder particle and the distribution of electrostatic charge over the electro-powder particle surface. FIG. 6 shows a first example of a prepared particle where the active substance 10 itself constitutes the electro-powder and the surface of a cross section presents a homogeneous structure, where electrostatic charges are well distributed over the surface.

Figure 7:
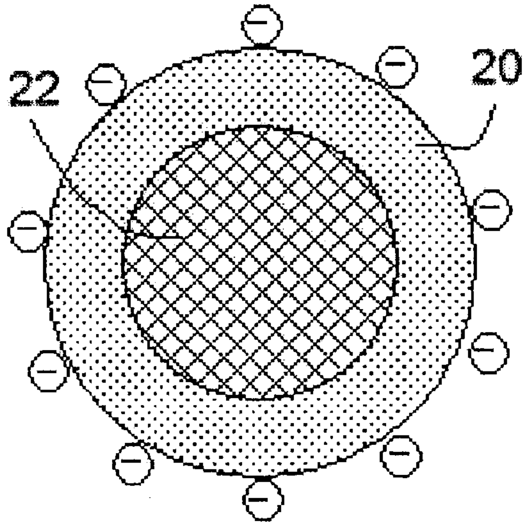
FIG. 7 illustrates in a cross section a second example of an electro-powder presenting an electrostatic charged surface.

The example of FIG. 7 shows a prepared electro-powder particle that consists of two components, active substance 22 coated with an excipient 20 presenting electrostatic charges distributed over the surface.

Figure 8:
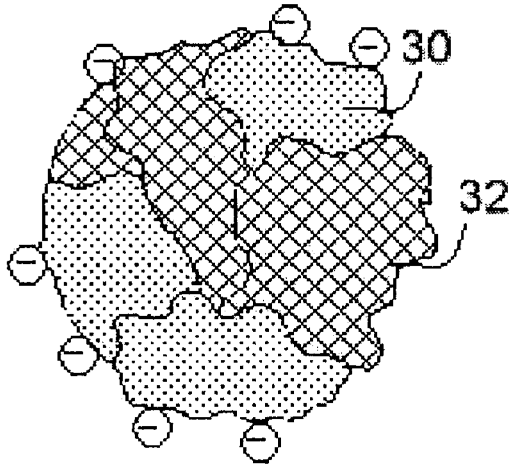
FIG. 8 illustrates in a cross section a third example of an electro-powder presenting an electrostatic charged surface of a section.

FIG. 8 shows yet a prepared electro-powder particle that is not homogeneous and consists of two components, an active substance 32 and an excipient 30, whereby the electrostatic charges are more distributed onto the excipient 30.

Figure 9:
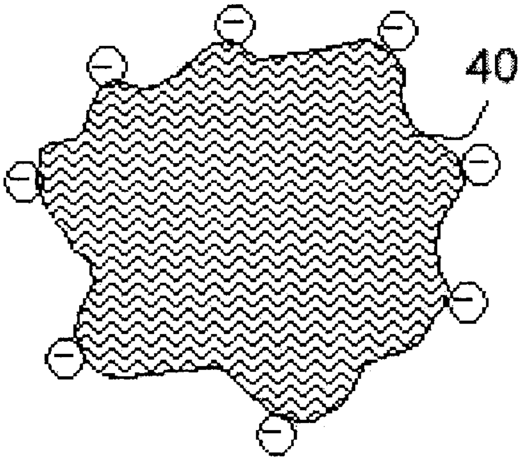
FIG. 9 illustrates in a cross section a fourth example of an electro-powder presenting an electrostatic charged surface.

FIG. 9 illustrates a prepared electro-powder presenting particles having a homogeneous mix of excipient and active substance 40 allowing the electrostatic charges to be distributed over the surface.

Figure 10:
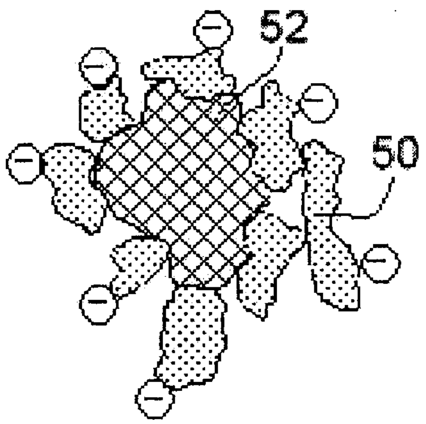
FIG. 10 illustrates in a cross section a fifth example of an electro-powder presenting an electrostatic charged surface.

FIG. 10 shows a prepared electro-powder particle where the active substance 52 and the excipient 50 are loosely attached and the electrostatic charges are mainly distributed at the excipient 50.

Figure 11:
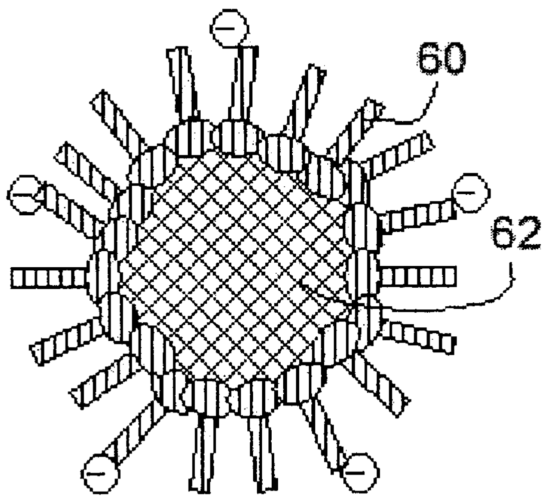
FIG. 11 illustrates in a cross section a sixth example of an electro-powder presenting an electrostatic charged surface.

FIG. 11 shows a prepared electro-powder in the form of a micelle or a liposome of an active substance 62 and an excipient 60 where the electrostatic charges are distributed over the surface of the excipient.

Figure 12:
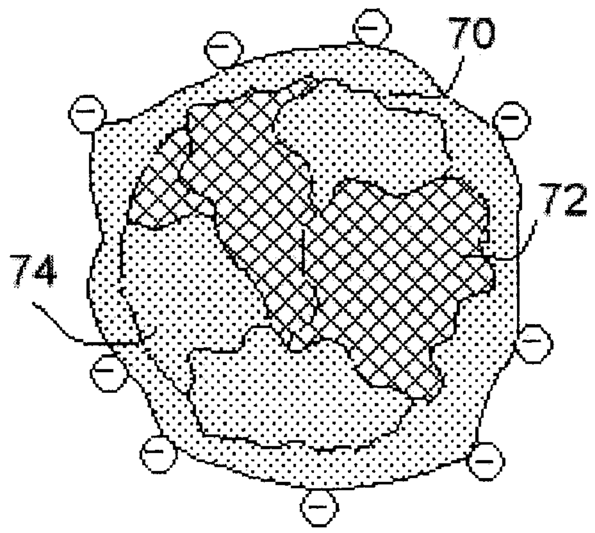
FIG. 12 illustrates in a cross section a seventh example of an electro-powder presenting an electrostatic charged surface.

FIG. 12 shows a prepared electro-powder particle in the form of multiple layered electro-powder consisting of a first mix of excipient 74 and active substance 72 and a second excipient 70 presenting distributed electrostatic charges over the surface.

Figure 13:
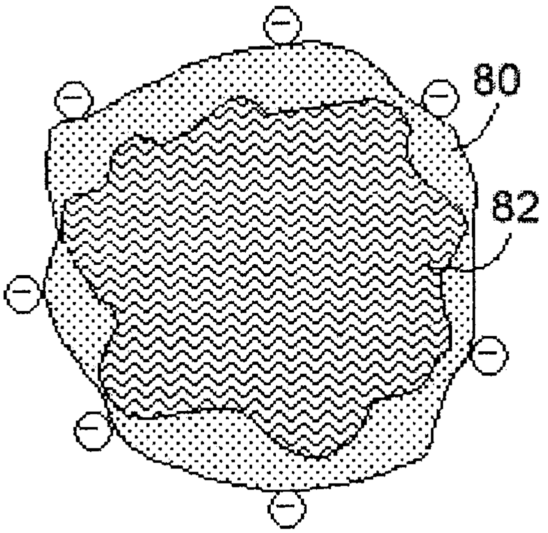
FIG. 13 illustrates in a cross section an eighth example of an electro-powder presenting an electrostatic charged surface.

Finally FIG. 13 shows a resulting electro-powder particle prepared as a multiple layer electro-powder consisting of a first homogenous mix of excipient and active substance 82 and a second excipient 80 showing distributed electrostatic charges over the surface. The excipient for achieving the desired electrostatic properties may be mixed in by the order of 2–50%, but to make a core (carrier) with substance the share of excipient mixed with the active substance 82 substituting the medicament as according to FIG. 13 may be much more, even of the order of $10^5$:1 in cases of administering medicaments with a very low dosage.

Below will be exemplified calculated results of preparations of electro-powder according to the process and method of the present invention.

EXAMPLE 1

The active substance 100 in example 1 was chosen as terbutalinesulphate (TBS) used for asthma treatment. The TBS in step 300, initially being in a powder form with a particle size distribution between 250–500 μm, was first micronized in step 310 in a manufacturing equipment like a device 400 of FIG. 4 or a device 500 of FIG. 5 to meet the powder specification for an electro-powder.

The TBS was then analyzed in the step 320 first measuring particle size in an Andersen impactor according to U.S. FDA (USP 24, NF 19 Supplement guidelines) at 28.3 liters/minute. The mass of powder was determined for instance by a chemical analysis using a HPLC according to the USP-24. A result of the Andersen impactor was then:

| Stage | μg |
|---|---|
| 0 | 10 |
| 1 | 15 |
| 2 | 13 |
| 3 | 20 |
| 4 | 25 |
| 5 | 30 |
| 6 | 49 |
| 7 | 20 |
| Filter | 15 |
| Total | 197 μg |

Result of particle size analysis in step 260 from stage 3 to 7 was a 73% fine particle fraction and that is better than the basic electro-powder specification demand stipulating >50% fine particle fraction.

The micronized TBS powder was then brought to the powder analyzing 320 for first analyzing the electrostatic charge in step 240 using for instance an Electrical Low Pressure Impactor (ELPI) model 3935 from DEKATI LTD.

The TBS substance was de-agglomerated and sucked into the instrument at 30 liters/minute and the total electrostatic charge in μC was measured together with an analysis of the powder mass sucked into the ELPI. Dividing the total electrostatic charge with the powder mass gives the specific charge in μC/g.

| | |
|---|---|
| Total electrostatic charge: | −6.2 nC |
| Total powder mass | 3.4 mg |
| Resulting measured specific charge = | −1.82 μC/g. |

Specific charge is also within electrical specification of an electro-powder as the measure −1.82 μC/g is within the absolute specific charge range $0.1\cdot10^{-6}$ to $25\cdot10^{-6}$ C/g set forth.

The TBS powder was then tested for its discharge rate (i.e. step 245 in FIG. 2) using the Electrical Low Pressure Impactor (ELPI). An analysis was set up with five consecutive tests at 5 different times to determine the discharge constant $Q_{50}$, the time until 50% of the electrostatic charge has been discharged having the TBS electrically isolated.

Discharge rate $Q_{50}$ for TBS in this preparation was 5 sec. $Q_{50}$ discharge rate of 5 sec is within the electro-powder specification stipulating the $Q_{50}$>0.1 sec.

| Analysis | Time (s) | Charge ($10^{-9}$ C) |
|---|---|---|
| 1 | 0 | −6.2 |
| 2 | 0.5 | −5.2 |
| 3 | 1 | −4.3 |
| 4 | 5 | −3.1 |
| 5 | 10 | −1.1 |

Thus TBS also constitutes an electro-powder in respect to the analysis of discharge at step 245.

TBS powder was now transferred to the chemical analysis. The first chemical analysis was water content at step 270 measured by a standard Karl-Fischer titration Mettler Toledo DL38 Titrator. Result of the five subsequent Karl-Fischer water content measurements gave

| | |
|---|---|
| 1 | 3.5% |
| 2 | 3.7% |
| 3 | 3.9% |
| 4 | 4.1% |
| 5 | 4.5 |
| Average | 3.94% |

The second chemical analysis was water activity at step 280 measured with a standard AquaLab model serie 3 TE at 24.3 C. Result of the five consecutive water activity measurements was:

| | |
|---|---|
| 1 | 0.35 |
| 2 | 0.37 |
| 3 | 0.38 |
| 4 | 0.36 |
| 5 | 0.37 |

giving then an average of 0.37.

The third chemical analysis for contamination at step 285 was performed with a standard HPLC SpectraSYSTEM with a UV 6000 detector. By the term contamination is understood any foreign substance or material not being an excipent or active substance in the powder. This measurement gives a guarantee that the manufacturing process of TBS has not introduced any contamination into the TBS powder. At step 290 a report of the result of the step of TBS powder analysis was reported and printed:

| Analysis | Specification | Result | Decision |
|---|---|---|---|
| Electrostatic charge | \|0.1–25 μC/g\| | −1.82 μC/g | Approved |
| Discharge rate | $Q_{50}$ > 0.1 sec | 5 sec | Approved |
| Powder mass | NA | 3.4 mg | Approved |
| Particle size | >50% < 5 μm | 73% | Approved |
| Water content | <4% | 3.94% | Approved |
| Water activity | $a_w$ < 0,5 | 0.37 | Approved |
| Contamination | acc. to FDA | not found | Approved |

This result approves that this TBS preparation will serve as an electro-powder for pre-prepared doses for a dry powder inhaler device, particularly an inhaler utilizing electrostatic principles for its operation.

EXAMPLE 2

The active substance nicotintartrate (NT) was tested for use in a DPI for smokers not allowed to smoke cigarettes due to medical reasons. The NT in step 300, initially being in powder form with a particle size distribution between 150–400 μm was first micronized in step 310 in a manufacturing equipment like device 400 of FIG. 4 or device 500 of FIG. 5 to meet the powder specification for an electro-powder.

The NT then was analyzed in step 320 in the Andersen Impactor at 28.3 liters/minute 260. The mass of powder was determined by chemical analysis using the HPLC SpectraSYSTEM.

Powder analysis of particle size resulted in the measures

| Stage | μg |
|---|---|
| 0 | 15 |
| 1 | 25 |
| 2 | 17 |
| 3 | 22 |
| 4 | 30 |
| 5 | 32 |
| 6 | 45 |
| 7 | 21 |
| Filter | 11 |
| Total | 218 μg |

Result of the particle size analysis in step 260 was for stages 3 to 7 a 69% fine particle fraction and that is more than our electro-powder specification demand stipulating >50% fine particle fraction.

The micronized NT powder then was brought to the powder analysis for analyzing first the electrostatic charge in step 240 using the Electrical Low Pressure Impactor (ELPI). The NT was de-agglomerated and sucked into the instrument at 30 liters/minute and the total electrostatic charge in μC was measured together with an analysis of the powder mass sucked into the ELPI using standard HPLC metods for NT. Dividing the total electrostatic charge with the powder mass gave the specific charge in μC/g.

| | | |
|---|---|---|
| Total electrostatic charge: | −0.17 | nC |
| Total powder mass | 4.3 | mg |
| Resulting measured specific charge = | −39.5 | nC/g. |

The specific charge of NT being −0.039 μC/g is then found to be too low a value to conform with our electro-powder electrical specification defining the absolute specific charge to be within the range of 100 nC/g to 25 μC/g. The conclusion is that NT has a poor value of specific charge and therefore not suitable to directly be used as an electro-powder.

There is no need for analyzing the discharge rate at step 245 for NT when the specific charge is not approved. The NT powder is transferred to chemical analysis of water content in step 270, water activity in step 280, and contamination in step 285.

First chemical analyzes of water content in step 270 was as before measured by the standard Karl-Fischer titration.

Result of the five consecutive water content measurements gave

| | |
|---|---|
| 1 | 3.8% |
| 2 | 3.5% |
| 3 | 3.7% |
| 4 | 3.5% |
| 5 | 3.5% |
| and an average of | 3.6%. |

The second chemical analysis was the water activity in step 280 measured with the AquaLab model series 3 TE at 24.3° C. yielding

| | |
|---|---|
| 1 | 0.43 |
| 2 | 0.41 |
| 3 | 0.42 |
| 4 | 0.44 |
| 5 | 0.42 |
| Calculated average | 0.42 |

The third chemical analyses was the contamination measurement in step 285 with a the HPLC SpectraSYSTEM.

At step 290 a report of the result of the NT powder analysis was reported and printed:

| Analysis of | Specification | Result | Decision |
|---|---|---|---|
| Electrostatic charge at 240 | \|0.1–25 μC/g\| | −0.039 μC/g | Not App. |
| Powder mass at 250 | NA | 4.3 mg | Approved |
| Particle size at 260 | >50% < 5 μm | 69% | Approved |
| Water content at 270 | <4% | 3.6% | Approved |
| Water activity at 270 | $a_w$ < 0.5 | 0.42 | Approved |
| Contamination at 285 | acc. to FDA | not found | Approved |

As a result of the powder analyzing the NT is transferred to the step 330 of determining preparation and manufacturing equipment together with an excipient and a new preparation has to be determined.

The following three preparations were suggested for further tests for the active substance NT.

| | Preparation | | |
|---|---|---|---|
| | #1 | #2 | #3 |
| Active substance NT | 90 | 75 | 50 |
| Excipient lactose α-monohydrate | 10 | 25 | 50 |
| Spray drying | one nozzle head | | |
| Solvent | Water/Methanol 50/50 | | |
| Particles configuration | FIG. 8 | | |

Preparation 1

The preparation #1 having 90% active substance and 10% excipient is analyzed first in the Andersen at 28.3 liters/minute. The mass of powder determined by chemical analyzes using the HPLC gives:

| Stage | μg |
|---|---|
| 0 | 11 |
| 1 | 17 |
| 2 | 12 |
| 3 | 24 |
| 4 | 25 |
| 5 | 32 |
| 6 | 45 |
| 7 | 22 |
| Filter | 18 |
| Total | 206 μg |

Result of particle size analysis is for stage 3 to 7 a 72% fine particle fraction, which is better than the electro-powder specification demand stipulating >50% fine particle fraction.

The preparation #1 is then brought to the powder analysis for analyzing first the electrostatic charge in step 240 using the Electrical Low Pressure Impactor (ELPI). The preparation 1 is de-agglomerated and sucked into the instrument at 30 liters/minute and the total electrostatic charge in μC is measured together with an analysis of the powder mass sucked into the ELPI. Dividing the total electrostatic charge with the powder mass will give the specific charge in μC/g.

| | | |
|---|---|---|
| Total electrostatic charge: | −0.34 | nC |
| Total powder mass | 3.8 | mg |
| Resulting measured specific charge = | −0.09 | μC/g. |

The preparation #1 then tested for discharge rate in step 245 using the Electrical Low Pressure Impactor (ELPI). The analysis is set up with five consecutive tests:

| Analyze | Time (s) | Charge ($10^{-9}$ C) |
|---|---|---|
| 1 | 0 | −0.9 |
| 2 | 1 | −0.5 |
| 3 | 5 | −0.3 |
| 4 | 10 | −0.2 |
| 5 | 25 | −0.0 |

The value of the discharge rate constant is found to be 2 sec for preparation #, and the preparation #1 is now transferred to chemical analysis being first the analysis of water content in step 270 measured by the Karl-Fischer titration.

Result of water content 270 analysis in step 270 then is

| | |
|---|---|
| 1 | 3.2% |
| 2 | 3.5% |
| 3 | 3.1% |
| 4 | 3.4% |
| 5 | 3.4% |
| Average | 3.32% |

The second chemical analysis is the water activity at step 280 measured with the AquaLab model series 3 TE at 24.3 C resulting in:

| | |
|---|---|
| 1 | 0.35 |
| 2 | 0.37 |
| 3 | 0.38 |
| 4 | 0.36 |
| 5 | 0.37 |
| Average | 0.37 |

The third chemical analysis is the contamination test in step 285 with the HPLC SpectraSYSTEM.

At step 290a report of the result of the preparation #1 powder analysis is reported and printed:

| Analysis | Specification | Result | Decision |
|---|---|---|---|
| Electrostatic charge | \|0.1–25 μC/g\| | −0.09 μC/g | Not App. |
| Discharge rate | $Q_{50}$ > 0.1 sec | 2 sec | Approved |
| Powder mass | NA | 3.8 mg | Approved |
| Particle size | >50% < 5 μm | 73% | Approved |
| Water content | <4% | 3.32% | Approved |
| Water activity | $a_w$ < 0.5 | 0.37 | Approved |
| Contamination | acc. to FDA | not found | Approved |

The result tells that the preparation #1 does not constitute an electro-powder.

Preparation #2

The preparation No 2 having a 75% active substance and 25% excipient is analyzed first in the Andersen 28.3 liters/minute. The mass of powder is determined by chemical analyzes using the HPLC.

| Stage | μg |
|---|---|
| 0 | 15 |
| 1 | 17 |
| 2 | 12 |
| 3 | 20 |
| 4 | 23 |
| 5 | 30 |
| 6 | 45 |
| 7 | 22 |
| Filter | 25 |
| | 209 μg |

Result of particle size analysis in step 260 is for stages 3 to 7 a 67% fine particle fraction which is higher than the minimum electro-powder specification demand stipulating >50% fine particle fraction.

The preparation #2 is then brought to the powder analyzing step 320 for analyzing first the electrostatic charge in step 240 using the Electrical Low Pressure Impactor (ELPI).

The preparation #2 was de-agglomerated and sucked into the instrument at 30 liters/minute and the total electrostatic charge in μC is measured together with an analyzing of the powder mass sucked into the ELPI. Dividing the total electrostatic charge with the powder mass gives the specific charge in μC/g.

| | |
|---|---|
| Total electrostatic charge: | −0.57 nC |
| Total powder mass | 4.3 mg |
| Resulting measured specific charge = | −0.133 μC/g. |

Then the preparation #2 is in consecutive measurement tested for discharge rate at step 245 using the Electrical Low Pressure Impactor (ELPI).

| Analyze | Time (s) | Charge ($10^{-9}$ C) |
|---|---|---|
| 1 | 0 | −3.2 |
| 2 | 1 | −2.1 |
| 3 | 5 | −1.1 |
| 4 | 10 | −0.4 |
| 5 | 25 | −0.1 |

The value of the discharge rate constant is >1 sec for preparation #2 and approved according to electrical specification of an electro-powder. The preparation #2 thereafter was transferred to the chemical analysis with the first analysis of water content in step 270 measured by the Karl-Fischer titration method.

Result of water content analysis in step 270 indicated

| | |
|---|---|
| 1 | 2.8% |
| 2 | 3.0% |
| 3 | 3.1% |
| 4 | 2.7% |
| 5 | 2.9% |
| Average | 2.9% |

The second chemical analysis is water activity in step 280 measured with the AquaLab instrument at 24.3° C. resulting in:

| | |
|---|---|
| 1 | 0.30 |
| 2 | 0.32 |
| 3 | 0.33 |
| 4 | 0.31 |
| 5 | 0.33 |
| Average | 0.32 |

The third chemical analysis is the contamination test in step 285 with the HPLC SpectraSYSTEM.

The result of the preparation #2 powder analysis is reported and printed at step 290:

| Analysis | Specification | Result | Decision |
|---|---|---|---|
| Electrostatic charge | \|0.1–25 μC/g\| | −0.13 μC/g | Approved. |
| Discharge | $Q_{50}$ > 0.1 sec | >1 sec | Approved |
| Powder mass | NA | 4.3 mg | Approved |
| Particle size | >50% < 5 μm | 67% | Approved |
| Water content | <4% | 2.9% | Approved |

-continued

| Analysis | Specification | Result | Decision |
|---|---|---|---|
| Water activity | $a_w < 0.5$ | 0.32 | Approved |
| Contamination | acc. to FDA | not found | Approved |

The result is that the preparation #2 is approved as an electro-powder.

Preparation #3

The preparation #3 is a preparation of 50% active substance and 50% excipient, which is analyzed first in the Andersen at 28.3 liters/minute. The mass of powder determined by chemical analyzes using the HPLC.

| Stage | μg |
|---|---|
| 0 | 20 |
| 1 | 17 |
| 2 | 23 |
| 3 | 28 |
| 4 | 31 |
| 5 | 32 |
| 6 | 35 |
| 7 | 26 |
| Filter | 20 |
| Total | 232 μg |

Result of particle size analysis in step 320 is for stages 3 to 7 a 66% fine particle fraction which is higher than the electro-powder specification demand stipulating >50% fine particle fraction.

The preparation #3 then was brought to the powder analyzing step 320 for analyzing first in step 240 the electrostatic charge using The Electrical Low Pressure Impactor. The preparation #3 was de-agglomerated and sucked into the instrument at 30 liters/minute and the total electrostatic charge in μC is measured together with an analyzing of the powder mass sucked into the ELPI. Dividing the total electrostatic charge with the powder mass gives the specific charge in μC/g.

| | |
|---|---|
| Total electrostatic charge: | −3.27 nC |
| Total powder mass | 4.3 mg |
| Result: Measured specific charge = | −0.76 μC/g |

The preparation #3 was then tested for discharge rate in step 245 using the ELPI. As before the analysis was set up with five consecutive tests

| Analysis | Time (s) | Charge ($10^{-9}$ C) |
|---|---|---|
| 1 | 0 | −5.8 |
| 2 | 1 | −4.3 |
| 3 | 5 | −3.4 |
| 4 | 10 | −1.8 |
| 5 | 25 | −0.3 |

The value of the discharge rate constant was found to be >5 sec for preparation #3 and the preparation #3 was now transferred to the chemical analysis steps 270–285 and the result of the water content analysis in step 270 was:

| | |
|---|---|
| 1 | 2.8% |
| 2 | 2.7% |
| 3 | 3.0% |
| 4 | 3.2% |
| 5 | 3.0% |
| Average | 2.9%. |

The second chemical analysis of water activity 280 measured with the AquaLab instrument at 24.3° C. then yielded:

| | |
|---|---|
| 1 | 0.33 |
| 2 | 0.35 |
| 3 | 0.37 |
| 4 | 0.39 |
| 5 | 0.34 |
| Average | 0.36. |

and finally the third chemical analysis for contamination in step 285 was performed with the HPLC SpectraSYSTEM.

The result of the preparation #3 powder analysis was reported and printed at step 290:

| Analysis | Specification | Result | Decision |
|---|---|---|---|
| Electrostatic charge | \|0.1–25 μC/g\| | −0.76 μC | Approved |
| Discharge rate | $Q_{50} > 0.1$ sec | >5 sec | Approved |
| Powder mass | NA | 4.3 mg | Approved |
| Particle size | >50% < 5 μm | 66% | Approved |
| Water content | <4% | 2.9% | Approved |
| Water activity | $a_w < 0.5$ | 0.36 | Approved |
| Contamination | acc. to FDA | not found | Approved |

The result was that the preparation #3 also constitutes an electro-powder.

Three different preparations where made and tested where preparation #1 did not meet the electrical specification for an electro-powder. Both preparations #2 and #3 did meet the specifications for an electro-powder and further test must determine which preparation is best suited for a nicotintartrate dry powder inhaler, DPI. However regarding the specific charge preparation #2 was found to be just within the lower limit but, rather close to preparation #1 which was not approved, while preparation #3 was found well within the given limits for electrostatic charge.

Being able to produce an electro-powder which will comply to the set of necessary desired parameters for the electrical field dosing technology will be a major breakthrough for inhalation of active substances to the upper and deep lung for both local lung treatments and for systemic delivery in complement to injection with needle.

It will be understood by those skilled in the art that various modifications and changes may be made to the present invention without departure from the scope thereof, which is defined by the appended claims.

What is claimed is:

1. A method for preparing electro-powder constituting micronized medical powder to be electrostatically charged by corona, induction or triboelectric charging and suitable for administration into the deep or upper lung airways by oral inhalation from a dry powder inhaler device, comprising the steps of:

selecting an active chemical or biological substance for conversion into an electro-powder;

micronizing and electrostatically charging the active substance for determining at least its electrostatic charging capacity and for determining a preparation and manufacturing equipment;

preparing a candidate electro-powder preparation in accordance with said electrostatic charging capacity using a selected preparation and manufacturing equipment;

analyzing the thereafter prepared candidate electro-powder preparation to verify that the obtained electro-powder has an electrostatic charging capacity rendering it suitable for utilization with a dry powder inhaler;

whereby, if the electro-powder is found not to possess said electrostatic charging capacity, the process is repeated with another manufacturing process to prepare a further candidate electro-powder preparation from the active substance.

2. The method according to claim 1, comprising the further steps of controlling the manufacture of the candidate electro-powder preparation to be a powder substance or dry powder medical formulation having a fine particle fraction (FPE) with 50% or more of particles between 0.5–5 $\mu$m and providing electrostatic properties regarding absolute specific charge per mass after charging of the order 0.1–25 $\mu$C/g and presenting a charge decay rate constant $Q_{50}$ of more than 0.1 sec.

3. The method according to claim 1, comprising the further step of preparing the candidate electro-powder preparation by a Fluid Jet Milling or a Spray Drying, a Cryo-technique or microwave techniques using raised temperature in the supplied air to dry the milled powder and as a result obtaining a water activity $a_w$ below 0.5.

4. The method according to claim 3, comprising the further step of analyzing the candidate electro-powder preparation by a Karl-Fisher method for a total analyzed water content to be below 4%.

5. The method according to claim 3, comprising the further step of transporting the candidate electro-powder preparation between a preparation process and a dosing unit with the electro-powder preparation being kept under vacuum.

6. The method according to claim 1, comprising the further step of selecting the active chemical or biological substance selected from the group consisting of vasopressin, a vasopressin analogue, desmopressin, glucagon, corticotropin, gonadotropin, calcitonin, C-peptide of insulin, parathyroid hormone, human growth hormone, growth hormone, growth hormone releasing hormone, oxytocin, corticotropin releasing hormone, a somatostatin analogue, a gonadotropin agonist analogue, atrial natriuretic peptide, thyroxine releasing hormone, follicle stimulating hormone, prolactin, an interleukin, a growth factor, a polypeptide vaccine, an enzyme, an endorphin, a glycoprotein, a lipoprotein, a kinase, intra-cellular receptors, transcription factors, gene transcription activators/repressors, neurotransmitters, proteoglycans, a polypeptide involved in the blood coagulation cascade that exerts its pharmacological effect systemically, any other polypeptide having a molecular weight (Daltons) of up to 50 kDa, proteins, polysaccharides, lipids, nucleic acids and combinations thereof, leuprolide and albuterol, opiates, nicotine, nicotine derivates, scopolamin, morphine, apomorphine analoges, pharmaceutical active chemicals for asthma treatment and salts thereof.

7. The method according to claim 1, comprising the further step of, in order to convert the active substance into a dry electro-powder, selecting and adding an excipient from a group consisting of polyvinyl alcohol, methalose, methyl cellulose, ethyl cellulose, propyl cellulose, hydroxy ethyl cellulose, carboxy methyl cellulose, polyoxyethylene cetyl ether, polyoxyethylene lauryl ether, polyoxyethylene octyl ether, polyoxyethylene octylphenyl ether, polyoxyethylene oleyl ether, polyoxyethylene sorbitan monolaurate, polyoxyethylene stearyl ether, polyoxyethylene nonylphenyl ether, and dialkylphenoxy poly(ethyleneoxy)ethanol sodium dodecyl sulfate, sodium dodecylbenzene sulfate and sodium dodecylnaphthalene sulfate glucolipids, phosphoglucolipids, a cationic surfactant dimethyl-β-cyclodextrin, dioctanoylphosphatidylcholine, lysophosphatidylcholine, a salt of caprate, laurate, oleate, myristate an anionic surfactant, a cationic surfactant, a phospholipid, an alkyl glycoside, a cyclodextrin, a salt of capric acid, a sodium, potassium or organic amine salt of a fatty acid, a bile salt, homo- and copolymers based on hydroxycarboxylic acids, polymers based on trioxanone, dioxanone (1,3 and 1,4), substituted dioxanone, trimethylene carbonate, ethylene carbonate, propylene carbonate, lactic acid, glycolic acid, pentaerythritol, sorbitol, adonitol, xylitol, fructose, epichlorohydrin, isopropyl-morpholine, isopropylmethylmorpholinedione, β-propionic acid, tetramethylglycolide, β-butyrolactone, butyrolactone, pivalolactone, α-hydroxybutyric acid, α-hydroxyisobutyric acid, α-hydroxyvaleric acid, α-hydroxyisovaleric acid, α-hydroxycaproic acid, α-hydroxyisocaproic acid, α-hydroxy-α-ethylbutyric acid, α-hydroxy-α-methylvaleric acid, α-hydroxyheptanoic acid, α-hydroxyoctanoic acid, α-hydroxydecanoic acid, α-hydroxytetradecanoic acid, α-hydroxystearic acid, a bio-degradable synthetic polymer, block copolymers poly(ethylene glycolaspartate, also named polymeric micelles a liposome forming substance, a natural or synthetic wax, sugar alcohols, monosaccarides, disaccarides, trisaccarides, polysaccarides, oligosaccarides, and buffering salts.

8. A method for preparing electro-powder constituting micronized medical powder to be electrostatically charged by corona, induction or triboelectric charging and suitable for administration into the deep or upper lung airways by oral inhalation from a dry powder inhaler device, comprising the steps of:

selecting a first active chemical or biological substance and a second active chemical or biological substance;

micronizing and electrostatically charging the first active substance for determining at least its electrostatic charging capacity with or without the second active substance for determining a preparation and manufacturing equipment;

preparing a candidate electro-powder preparation in accordance with said electrostatic charging capacity using a selected preparation and manufacturing equipment;

analyzing the thereafter prepared candidate electro-powder preparation to verify that the obtained electro-powder has an electrostatic charging capacity rendering it suitable for utilization with a dry powder inhaler;

whereby, if the electro-powder is found not to possess said electrostatic charging capacity, the process is repeated with another manufacturing process to prepare a further candidate electro-powder preparation from the active substance.

9. A method for preparing electro-powder constituting micronized medical powder to be electrostatically charged by corona, induction or tribo-electric charging and suitable for administration into the deep or upper lung airways by oral inhalation from a dry powder inhaler device, comprising the steps of:

inserting into a process of at least one active chemical or biological substance in combination with an excipient in order to convert the active substance into an electro-powder;

micronizing and electrostatically charging the active substance for determining at least its electrostatic charging capacity for determining a preparation and manufacturing equipment;

preparing a candidate electro-powder preparation in accordance with said electrostatic charging capacity by means of a selected preparation and manufacturing equipment;

analyzing the thereafter prepared candidate electro-powder preparation to verify that the obtained electro-powder has an electrostatic charging capacity rendering it suitable for utilization with a dry powder inhaler;

whereby, if the electro-powder is found not to possess said electrostatic charging capacity, the process is repeated for finding another manufacturing process for an operating preparation of the active substance.

* * * * *